United States Patent
Mukousaka et al.

(10) Patent No.: US 10,416,130 B2
(45) Date of Patent: Sep. 17, 2019

(54) MASS SPECTROMETRY DATA PROCESSING APPARATUS, MASS SPECTROMETRY SYSTEM, AND METHOD FOR PROCESSING MASS SPECTROMETRY DATA

(71) Applicant: JEOL Ltd., Tokyo (JP)

(72) Inventors: Shinichi Mukousaka, Tokyo (JP); Yoshiyuki Ito, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 16/003,425

(22) Filed: Jun. 8, 2018

(65) Prior Publication Data

US 2018/0356377 A1    Dec. 13, 2018

(30) Foreign Application Priority Data

Jun. 12, 2017  (JP) .................. 2017-115001

(51) Int. Cl.
  *G01N 30/72*  (2006.01)
  *G01N 30/86*  (2006.01)
  *H01J 49/40*  (2006.01)
  *H01J 49/00*  (2006.01)
  *G01N 30/00*  (2006.01)

(52) U.S. Cl.
  CPC ......... *G01N 30/72* (2013.01); *G01N 30/8617* (2013.01); *G01N 30/8631* (2013.01); *H01J 49/0036* (2013.01); *H01J 49/40* (2013.01); *G01N 2030/0085* (2013.01)

(58) Field of Classification Search
  None
  See application file for complete search history.

(56) References Cited

U.S. PATENT DOCUMENTS

| | | | | |
|---|---|---|---|---|
| 6,008,490 A | * | 12/1999 | Kato | H01J 49/0036 250/282 |
| 6,863,790 B1 | * | 3/2005 | Moini | H01J 49/167 204/452 |
| 7,684,934 B2 | * | 3/2010 | Shvartsburg | H01J 49/04 702/27 |
| 2005/0061967 A1 | * | 3/2005 | Shvartsburg | H01J 49/04 250/288 |
| 2005/0227321 A1 | * | 10/2005 | Krebs | C07K 14/4723 435/69.1 |

FOREIGN PATENT DOCUMENTS

| | | | |
|---|---|---|---|
| JP | 201392495 A | | 5/2013 |
| JP | 2013092495 A | * | 5/2013 |

* cited by examiner

*Primary Examiner* — Andrew Smyth
(74) *Attorney, Agent, or Firm* — The Webb Law Firm

(57) ABSTRACT

A mass spectrometry data processing apparatus includes a computation unit and a seeking unit. The computation unit calculates the mass difference Δm/z between the peaks of two molecules selected from mass spectrum data or obtains the mass difference Δm/z. The seeking unit estimates a combination of atoms between the peaks of the two molecules in a range of the mass difference Δm/z. The seeking unit seeks the combination of atoms having a mass difference, which matches the mass difference Δm/z, between a set of atoms desorbed from a first molecule of the two molecules and a set of atoms added to the first molecule.

6 Claims, 7 Drawing Sheets

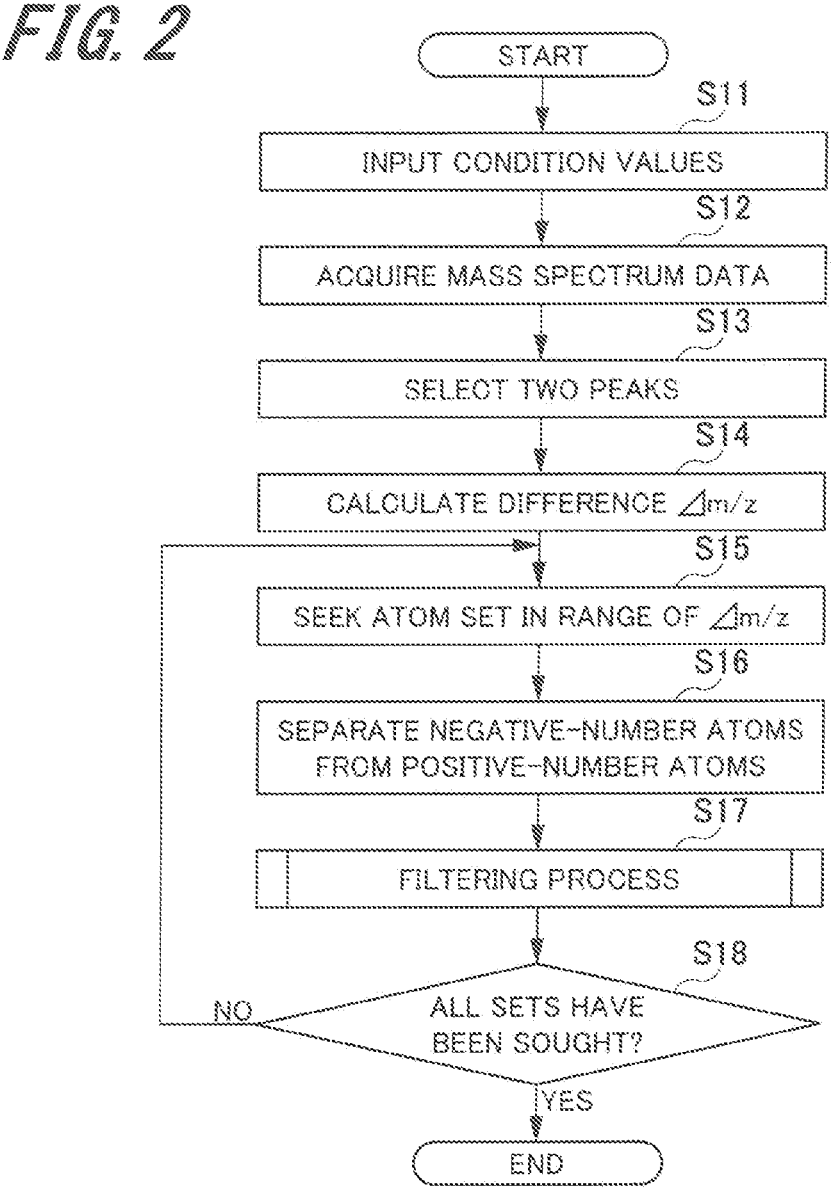

FIG. 3

| | COMPOSITION ESTIMATION ACCORDING TO EXAMPLE OF RELATED ART | COMPOSITION ESTIMATION ACCORDING TO PRESENT EMBODIMENT |
|---|---|---|
| ERROR IN m/z | ±0.01u | ±0.01u |
| DBE RANGE | -1.5 ~ 25.0 | -1.5 ~ 25.0 |
| THE NUMBER OF ELECTRONS | Odd | - |
| CHARGE | +1 | - |
| RANGE OF THE NUMBER OF CARBON ATOMS (C) | 0 ~ 100 | -6 ~ +100 |
| RANGE OF THE NUMBER OF HYDROGEN ATOMS (H) | 0 ~ 200 | -15 ~ +200 |
| RANGE OF THE NUMBER OF OXYGEN ATOMS (O) | 0 ~ 15 | -2 ~ +15 |
| RANGE OF THE NUMBER OF NITROGEN ATOMS (N) | 0 ~ 10 | -4 ~ +10 |
| RANGE OF THE NUMBER OF PHOSPHORUS ATOMS (P) | 0 ~ 2 | 0 ~ +2 |

MASS SPECTROMETRY DATA PROCESSING APPARATUS, MASS SPECTROMETRY SYSTEM, AND METHOD FOR PROCESSING MASS SPECTROMETRY DATA

CROSS-REFERENCE TO RELATED APPLICATION

This application claims priority to Japanese Patent Application No. 2017-115001 filed Jun. 12, 2017, the disclosure of which is hereby incorporated in its entirety by reference.

BACKGROUND OF THE INVENTION

Field of the Invention

The present invention relates to a mass spectrometry data processing apparatus, a mass spectrometry system, and a method for processing mass spectrometry data, which are used to analyze an introduced sample.

Description of Related Art

Until now, in mass spectrometry data processing apparatuses, processing of various data has been performed by using mass spectra obtained through analysis using a mass spectrometer. For example, in a mass spectrometry data processing apparatus, the composition of a molecule whose composition is unknown is estimated from a peak value in mass spectrum data. The composition is estimated by seeking combinations of atoms from the peak value (accurate mass) of a target molecule. Therefore, an increase in the accurate mass value of the target molecule results in an enormous number of combinations of atoms, making it difficult to filter candidates.

Japanese Unexamined Patent Application Publication No. 2013-92495 describes a technique in which the mass differences between any ion and the other ions which are detected in a mass spectrum are detected, and in which selection is performed from a group of ions whose mass difference matches a combination of desired molecules.

However, the technique described in Japanese Unexamined Patent Application Publication No. 2013-92495 is a technique for determining an ion whose mass difference from the selected ion matches a combination of desired molecules. The composition between the peaks of any two molecules based on mass spectrum data is not estimated.

SUMMARY OF THE INVENTION

The present invention is made in consideration of the problem described above, and an object of the present invention is to provide a mass spectrometry data processing apparatus, a mass spectrometry system, and a method for processing mass spectrometry data, which enable the composition between the peaks of any two molecules based on mass spectrum data to be estimated.

To address the above-described issue and achieve the object of the present invention, the present invention provides a mass spectrometry data processing apparatus including a computation unit and a seeking unit. The computation unit calculates a mass difference between peaks of two molecules selected from mass spectrum data or obtains the mass difference. The seeking unit estimates a combination of atoms between the peaks of the two molecules. The estimation is performed in a range of the mass difference. The seeking unit seeks the combination of atoms. The combination has a mass difference matching the mass difference between the peaks of the two molecules. The mass difference of the combination is a mass difference between a set of atoms desorbed from a first molecule of the two molecules and a set of atoms added to the first molecule.

A mass spectrometry system includes a mass spectrometer and a mass spectrometry data processing apparatus. The mass spectrometer performs mass spectrometry on a sample and generates mass spectrum data. The mass spectrometry data processing apparatus obtains the mass spectrum data from the mass spectrometer. As the mass spectrometry data processing apparatus, the mass spectrometry data processing apparatus described above is used.

The present invention provides a method for processing mass spectrometry data. The method includes the processes (1) and (2) described below.

(1) The process of calculating a mass difference between peaks of two molecules selected from mass spectrum data or obtaining the mass difference.

(2) The process of estimating a combination of atoms between the peaks of the two molecules. The estimation is performed in a range of the mass difference.

In the estimation process, the combination of atoms is sought. The combination has a mass difference matching the mass difference between the peaks of the two molecules. The mass difference of the combination is a mass difference between a set of atoms desorbed from a first molecule of the two molecules and a set of atoms added to the first molecule.

The mass spectrometry data processing apparatus, the mass spectrometry system, and the method for processing mass spectrometry data, which are provided by the present invention, enable the composition between the peaks of any two molecules to be estimated.

BRIEF DESCRIPTION OF THE DRAWINGS

FIG. 2 is a flowchart of a method for processing mass spectrometry data according to an exemplary embodiment.

FIG. 3 is a diagram illustrating a table indicating condition values for a method for processing mass spectrometry data according to an exemplary embodiment and for an example of the related art.

DESCRIPTION OF THE INVENTION

Figure 1:
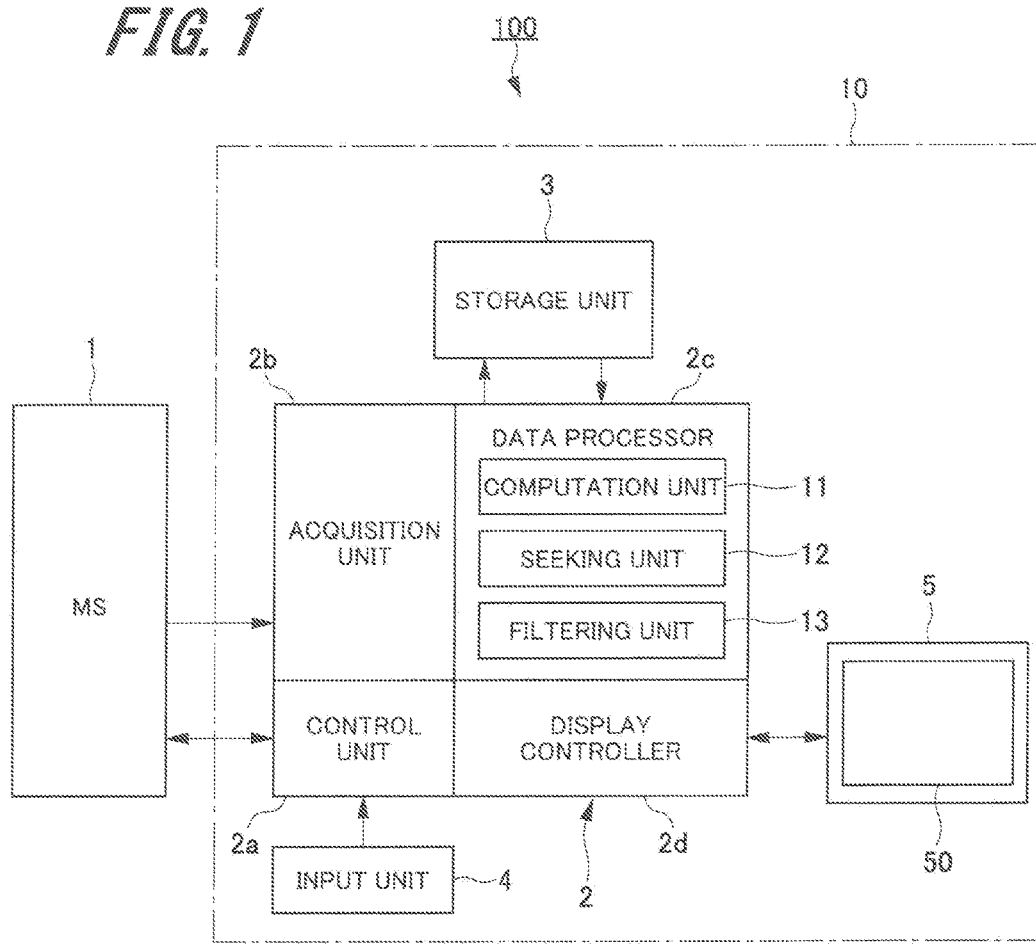
FIG. 1 is a block diagram illustrating a mass spectrometry system according to an exemplary embodiment.

An exemplary embodiment of a mass spectrometry data processing apparatus, a mass spectrometry system, and a method for processing mass spectrometry data, which are provided by the present invention, will be described below by referring to FIGS. 1 to 7. In the figures, common components are designated with identical reference characters. The description will be made in the order as described below. However, the present invention is not necessarily limited to the embodiment described below.

The Configuration of a Mass Spectrometry System

A mass spectrometry system according to an exemplary embodiment (hereinafter referred to as the "present embodiment") of the present invention will be described by referring to FIG. 1.

FIG. 1 is a block diagram illustrating the configuration of the mass spectrometry system according to the present embodiment.

A mass spectrometry system 100 illustrated in FIG. 1 is used to analyze an introduced sample. As illustrated in FIG. 1, the mass spectrometry system 100 includes a mass spectrometer (MS) 1 and a mass spectrometry data processing apparatus 10. The mass spectrometer 1 and the mass spectrometry data processing apparatus 10 are connected to each other over a wireless or wired network (a local area network (LAN), the Internet, a leased line, or the like), and are capable of receiving/transmitting data from/to each other.

The mass spectrometer 1 is an apparatus which ionizes the introduced sample, detects the detected intensity for each ion mass-to-charge ratio (m/z), and generates mass spectrum data. The mass spectrometer 1 includes an ion source that ionizes the introduced sample, a mass separator that separates the ions, which are generated by the ion source, in accordance with their masses, and a detection unit that detects the ions having been separated by the mass separator.

As an ionization method used by an ion source, various ionization methods, such as the electron ionization (EI) method, the chemical ionization (CI) method, the fast atom bombardment (FAB) method, the electrospray ionization (ESI) method, the atmospheric pressure chemical ionization (APCI) method, and the matrix-assisted laser desorption/ionization (MALDI) method, may be applied. As the ionization method used by the ion source according to the present embodiment, the MALDI method is used.

As a mass separator, various mass separators, such as the magnetic type, the quadrupole type, the ion trap type, the Fourier transform ion cyclotron resonance type, the time-of-flight type, and a combination of some of these, may be applied. The time-of-flight type is used as the mass separator according to the present embodiment.

The detection unit converts the detected intensities of the detected ions into a digital signal, and transmits the resulting signal to a controller 2 of the mass spectrometry data processing apparatus 10.

The mass spectrometry data processing apparatus 10 includes the controller 2, a storage unit 3, an input unit 4, and a display device 5. The controller 2 includes a control unit 2a that exerts control on the mass spectrometer 1, an acquisition unit 2b that acquires mass spectrometry data from the mass spectrometer 1, a data processor 2c, and a display controller 2d that exerts control on the display device 5.

The control unit 2a is connected to the input unit 4. As the input unit 4, various input units, such as a keyboard and a switch, are applied. The acquisition unit 2b acquires mass spectrum data from the mass spectrometer 1. The acquisition unit 2b transmits the acquired mass spectrometry data to the data processor 2c.

The data processor 2c performs computation on the acquired mass spectrometry data. The data processor 2c includes a computation unit 11, a seeking unit 12, and a filtering unit 13. The computation unit 11 performs computation on the mass spectrometry data acquired by the acquisition unit 2b. The seeking unit 12 estimates the composition in accordance with information obtained through computation performed by the computation unit 11, information received through the input unit 4, and information stored in the storage unit 3.

The filtering unit 13 filters the composition candidates, which are found by the seeking unit 12, in accordance with preset conditions. The filtering unit 13 transmits the filtered composition candidates to the display controller 2d and the storage unit 3.

The display controller 2d performs a process for displaying, on the display device 5, data obtained through computation performed by the data processor 2c, mass spectrometry data obtained by the acquisition unit 2b, and the like.

The storage unit 3 stores various data transmitted from the controller 2, and also stores accurate masses, as mass-to-charge ratios (m/z values), of elements used in the composition estimation.

As the mass spectrometry data processing apparatus 10, a control apparatus integrated with the mass spectrometer 1 may be applied. Alternatively, an external portable information processing terminal, a personal computer (PC), or the like may be applied.

A Data Processing Method Using the Mass Spectrometry System

An exemplary data processing method (composition estimating process) using the mass spectrometry system 100 having the configuration described above will be described by referring to FIGS. 2 to 6.

Figure 4:
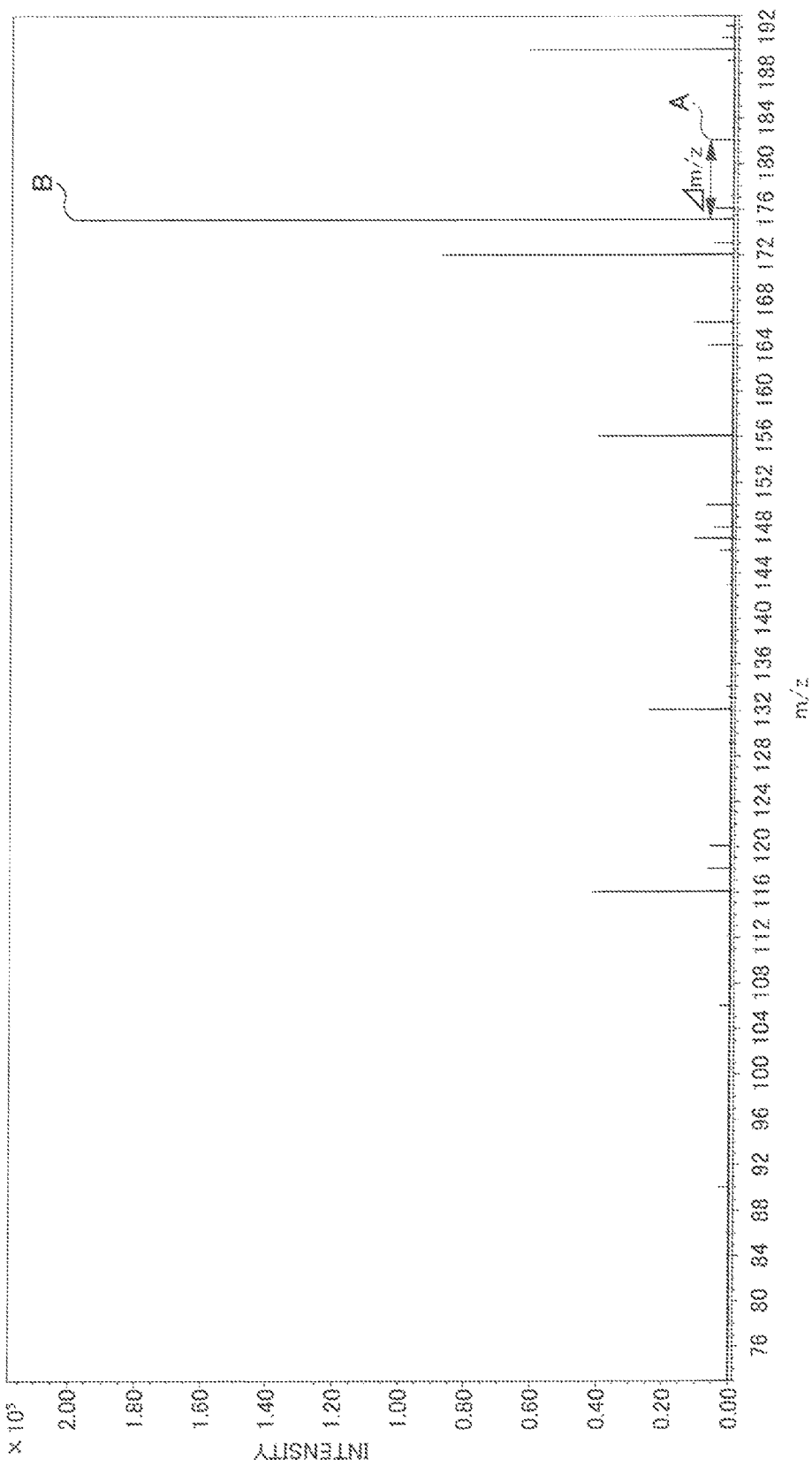
FIG. 4 is a diagram illustrating exemplary mass spectrum data used in a method for processing mass spectrometry data, according to an exemplary embodiment.
Figure 5:
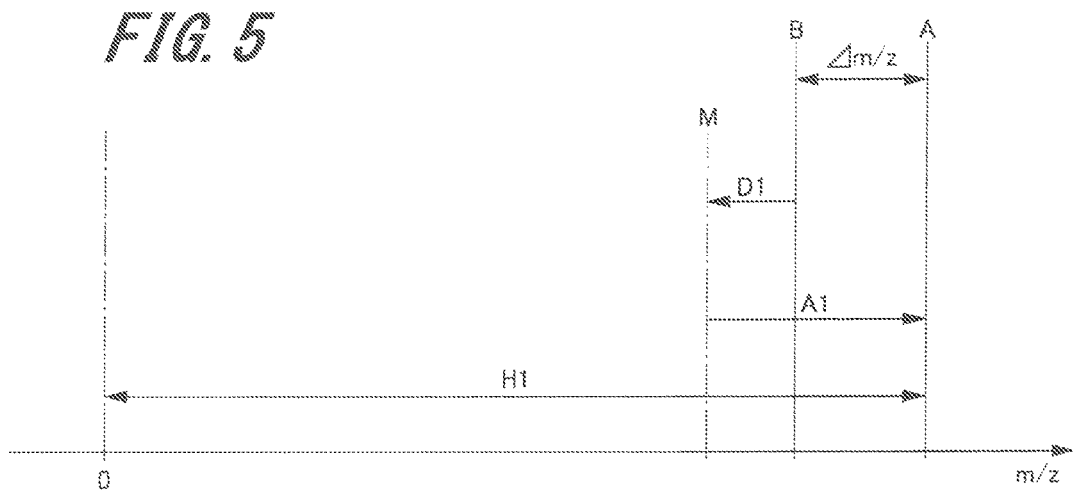
FIG. 5 is a diagram for describing an overview of a method for processing mass spectrometry data, according to an exemplary embodiment.

FIG. 2 is a flowchart of a data processing method. FIG. 3 illustrates a table indicating condition values used in the data processing method. FIG. 4 illustrates mass spectrum data used in the data processing method. FIG. 5 is a diagram for describing an overview of the data processing method according to the present embodiment.

As illustrated in FIG. 2, a user inputs condition values through the input unit 4 (step S11). Examples of the condition values which are input in step S11 include the "error in mass (m/z)", the "DBE value range" used in a filtering process, the element types used in seeking a combination (composition estimation), and the "minimum" and the "maximum" of the number of atoms of each element type, which are indicated in the table in FIG. 3. In a data processing method of the related art, "the number of electrons" and the "charge" which are used in a filtering process are also input. The condition values which are input through the input unit 4 are stored in the storage unit 3.

In the present embodiment, the example in which a user inputs condition values through the input unit 4 is described. However, this is not limiting. For example, the condition values indicated in FIG. 3 are stored in the storage unit 3 in advance. In data processing, the data processor 2c of the controller 2 may obtain the condition values from the storage unit 3.

The acquisition unit 2b of the controller 2 acquires mass spectrum data from the mass spectrometer 1 (step S12). Step S12 of acquiring mass spectrum data may be performed before step S11 of inputting condition values.

Then, peaks (monoisotopic peaks) of two molecules are selected from the mass spectrum data (step S13). In step S13, for example, the mass spectrum illustrated in FIG. 4 is displayed on the display device 5, and a user selects the peaks A and B of two molecules, between which the difference is to be subjected to composition estimation. Alternatively, the mass-to-charge ratios (m/z values) of the peaks of two molecules, between which the difference is to be subjected to composition estimation, or their accurate masses may be input through the input unit 4.

The data processor 2c extracts mass-to-charge ratios (m/z values) of the two selected peaks A and B, that is, the accurate masses of any two molecules. The computation unit 11 of the data processor 2c calculates the difference (mass difference) between the accurate masses of the two molecules (step S14). Specifically, the computation unit 11 calculates Δm/z which is the difference between the m/z values at the two selected peaks A and B (step S14). The computation unit 11 may obtain the mass difference Δm/z through the acquisition unit 2b or the input unit 4. The mass difference Δm/z calculated by the computation unit 11 is stored in the storage unit 3, and, at the same time, is output to the seeking unit 12.

The seeking unit 12 seeks a combination of atoms (hereinafter simply referred to as a "set") in the range of the mass difference Δm/z in accordance with the condition values received in step S11 and the accurate masses of elements which are used in seeking a combination and which are stored in the storage unit 3 (step S15).

As illustrated in FIG. 5, not only adduct atoms but also desorption atoms are present between the peak A and the peak B. The accurate mass (mass-to-charge ratio) of the subset of atoms (subset of negative-number atoms) desorbed from the selected peak B is defined as the desorption mass D1. The accurate mass (mass-to-charge ratio) of the subset of atoms (subset of positive-number atoms) added from the peak B is defined as the adduct mass A1. In this case, A1−D1=Δm/z. Therefore, the seeking unit 12 seeks an atom set in which the difference between the desorption mass D1 and the adduct mass A1 matches the mass difference Δm/z.

The element types and the maximum and the minimum of the number of atoms of each element type, which are used in the seeking process in step S15, are condition values which are illustrated in FIG. 3 and which are input in step S11.

In a data processing method of the related art, an atom set is sought in the m/z value range H1 from 0 to the peak A of a molecule whose composition is to be estimated. Therefore, as illustrated in FIG. 3, the condition values used in an exemplary data processing method of the related art are input as follows. An integer which is equal to or larger than 0 and which is not a negative number less than 0 is input as the number of atoms which is used in seeking a combination, and the "minimum" is equal to 0. Further, in a data processing method of the related art, as illustrated in FIG. 5, the range H1 in which seeking is performed is wide. Therefore, a large error occurs in the composition estimation.

In contrast, in the data processing according to the present embodiment, an atom set is sought in the range of the mass difference Δm/z between the two peaks A and B. As described above, the seeking unit 12 which performs data processing according to the present embodiment seeks an atom set also in consideration of desorption atoms. Thus, the composition for the difference between the peaks of any two molecule may be estimated.

Desorption atoms are also considered. Accordingly, as illustrated in FIG. 3, the condition values which are input in step S11 are set as follows. The "minimum" of the number of atoms may be set to a negative number, that is, a number equal to or less than 0. According to the present embodiment, the settings are made as follows: the number of Cs ranges from −6 to +100 (the minimum is −6, and the maximum is +100); the number of Hs ranges from −15 to +200 (the minimum is −15, and the maximum is +200); the number of Os ranges from −2 to +15 (the minimum is −2, and the maximum is 15); the number of Ns ranges from −4 to +10 (the minimum is −4, and the maximum is +10); and the number of Ps ranges from 0 to +2 (the minimum is 0, and the maximum is +2). The accurate masses of these elements are stored in the storage unit 3 in advance. The element types and the range of the number of atoms of each element type may be changed to any values in accordance with a composition estimation target.

In the data processing method according to the present embodiment, the range in which an atom set is sought is set between the two peaks A and B. Therefore, the search range may be made smaller than the range H1 in a data processing method of the related art, and a smaller error may occur in the composition estimation. Further, the range for the composition estimation is made smaller. Therefore, the number of combinations of atoms may be decreased, and candidates may be easily filtered.

For example, when the composition of tyrosine is to be estimated, the accurate mass of tyrosine, that is, the measured m/z value, is 182.08117. Therefore, the m/z value of the range for composition estimation of an example of the related art is 182.08117.

In contrast, assume that, in the data processing according to the present embodiment, the composition for the difference between tyrosine and arginine is estimated. In this case, the peak value of tyrosine is selected as the peak A, and the peak value of arginine is selected as the peak B. The accurate mass of arginine, that is, the measured m/z value, is 175.11889. The mass difference Δm/z between tyrosine and arginine is 6.96228. Therefore, the m/z value of the range for composition estimation in the data processing method according to the present embodiment is 6.96228. It is found that the range is made smaller than the above-described range for composition estimation of the related art.

The seeking unit 12 outputs the found atom set to the display controller 2d, the filtering unit 13, the storage unit 3, and the like. An atom set which is output from the seeking unit 12 is an atom set in which a subset of negative-number atoms and a subset of positive-number atoms are present. For example, when the seeking unit 12 outputs an atom set of C3H-3O1N-3, this set indicates that three Cs and one O are added and that three Hs and three Ns are desorbed.

The data processor 2c separates the subset of negative-number atoms, which is a subset of desorption atoms, from the subset of positive-number atoms, which is a subset of adduct atoms, in the found atom set (step S16). In the process in step S15, for example, if an atom set of C3H-3O1N-3 is found, H3 and N3 are separated as a subset of negative-number atoms, and C3 and O1 are separated as a subset of positive-number atoms.

The filtering unit 13 performs the filtering process based on the subset of negative-number atoms and the subset of positive-number atoms which are obtained through separation in step S16 (step S17). According to the present embodiment, the example in which a subset of negative-number atoms is separated from a subset of positive-number atoms is described. However, this is not limiting. The filtering process may be performed by using an atom set in which a subset of negative-number atoms and a subset of positive-number atoms are present.

Filtering Process

Figure 6:
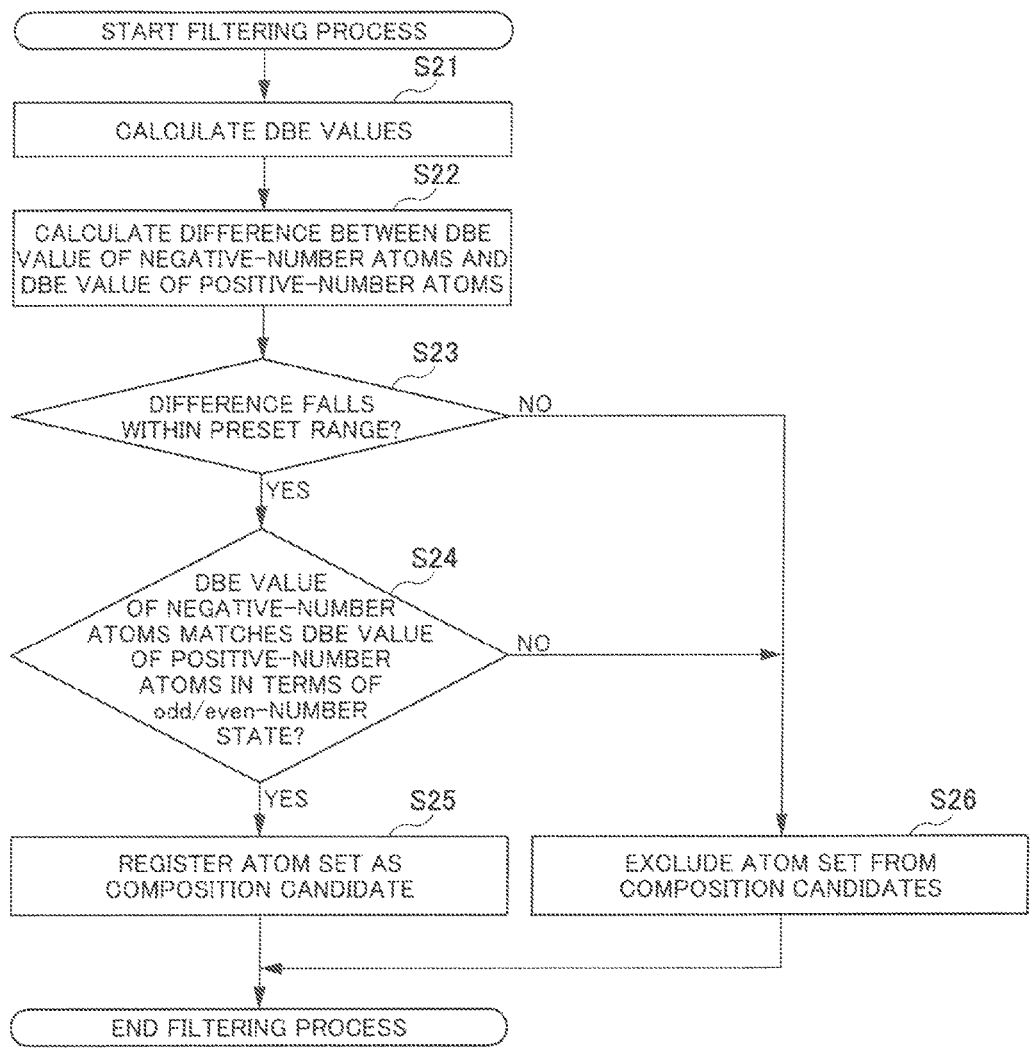
FIG. 6 is a flowchart of a filtering process in a method for processing mass spectrometry data, according to an exemplary embodiment.

Referring to FIG. 6, an exemplary filtering process in step S17 will be described.

FIG. 6 is a flowchart of an exemplary filtering process.

As illustrated in FIG. 6, the filtering unit 13 calculates the double bond equivalent (DBE) value of the subset of negative-number atoms and the DBE value of the subset of positive-number atoms (step S21). The subset of negative-number atoms has been separated from the subset of positive-number atoms in step S16. That is, in step S21, the degree of unsaturation of the subset of negative-number atoms and the degree of unsaturation of the subset of positive-number atoms are calculated.

A DBE value is calculated by using Expression 1, which is described below, where, in an atom set, the number of carbon atoms is represented by w; the number of hydrogen atoms is represented by x; the number of halogen atoms is represented by y; and the number of nitrogen atoms is represented by z. Group elements, such as oxygen and sulfur, are not counted. However, hydrogen elements bound to oxygen atoms, such as a hydroxy group, are counted.

$$DBE=(2+2w-x-y+z)/2 \qquad \text{Expression 1}$$

For example, when an atom set of C3H-3O1N-3 is found, H3 and N3 are separated as a subset of negative-number atoms, and C3 and O1 are separated as a subset of positive-number atoms. Therefore, the DBE value of the subset of negative-number atoms is 1 from $(2-3+3)/2$. The DBE value of the subset of positive-number atoms is 4 from $(2+2\times3)/2$.

The filtering unit 13 calculates the difference between the DBE value of the subset of negative-number atoms and the DBE value of the subset of positive-number atoms (step S22). These DBE values are calculated in step S21. If the DBE value of the subset of negative-number atoms is 1 and the DBE value of the subset of positive-number atoms is 4, the difference between the DBE values is 3 from 4−1.

The filtering unit 13 determines whether or not the difference between the DBE values which is calculated in step S22 falls within the range which is set in step S11 (step S23). The range used in this step is the "DBE range" illustrated in FIG. 3. In the present embodiment, the range is set to −1.5 to 25.0. The DBE range may be changed to any value in accordance with a composition estimation target.

In step S23, if the filtering unit 13 determines that the difference between the DBE values does not fall within the range (NO in step S23), the filtering unit 13 excludes, from the composition candidates, the atom set which is being subjected to the filtering process (step S26). The filtering process is completed, and the process returns to step S18 illustrated in FIG. 2.

In contrast, in step S23, if the filtering unit 13 determines that the difference between the DBE values falls within the range (YES in step S23), the filtering unit 13 determines whether or not the DBE value of the subset of negative-number atoms matches the DBE value of the subset of positive-number atoms in terms of the odd/even-number state (step S24).

The even-numbered state indicates that all of the bonds (valence) are bound. The odd-numbered state indicates that a bond which is not bound to an atom is present. A DBE value is obtained through division by 2, as illustrated in Expression 1. Therefore, an integer indicates the even-numbered state, and a value obtained by adding 0.5 to an integer indicates the odd-numbered state.

As described above, in the atom set of C3H-3O1N-3, the DBE value of the subset of negative-number atoms is 1, and the DBE value of the subset of positive-number atoms is 4. Thus, the DBE value of the subset of negative-number atoms is an integer, and the DBE value of the subset of positive-number atoms is also an integer. Accordingly, it may be determined that the valence state of the subset of desorption atoms matches the valence state of the subset of adduct atoms.

The example in which it is determined whether or not the DBE value of a subset of negative-number atoms matches the DBE value of a subset of positive-number atoms in terms of the odd/even-number state in step S24 according to the present embodiment is described. However, this is not limiting. When the DBE value of a subset of negative-number atoms matches the DBE value of a subset of positive-number atoms in terms of the odd/even-number state, subtraction of the DBE value of a subset of negative-number atoms from the DBE value of a subset of positive-number atoms always results in an integer. In contrast, if the odd/even-number states are different from each other, the result is always a half-integer, that is, a value obtained by adding 0.5 to an integer. Therefore, the same determination as that in step S24 may be made by subtracting the DBE value of a subset of negative-number atoms from the DBE value of a subset of positive-number atoms.

In step S24, if the filtering unit 13 determines that the DBE value of the subset of negative-number atoms does not match the DBE value of the subset of positive-number atoms in terms of the odd/even-number state (NO in step S24), the filtering unit 13 excludes, from the composition candidates, the atom set which is being subjected to the filtering process (step S26). The filtering process is completed, and the process returns to step S18 illustrated in FIG. 2.

In contrast, in step S24, if the filtering unit 13 determines that the DBE value of the subset of negative-number atoms matches the DBE value of the subset of positive-number atoms in terms of the odd/even-number state (YES in step S24), the filtering unit 13 registers the atom set, which is being subjected to the filtering process, as a composition candidate (step S25). That is, the filtering unit 13 stores, in the storage unit 3, the atom set which is being subjected to the filtering process. Thus, the filtering process performed by the filtering unit 13 is completed, and the process returns to step S18 illustrated in FIG. 2.

As illustrated in FIG. 2, the data processor 2c determines whether or not the seeking unit 12 has sought all of the atom sets in the range of the mass difference Δm/z (step S18). In step S18, if the data processor 2c determines that the seeking process has not been completed (NO in step S18), the process returns to step S15, and the process of seeking an atom set is continued.

In step S18, if the data processor 2c determines that all of the atom sets have been sought (YES in step S18), the display controller 2d causes the display device 5 to display the atom set candidates which are obtained through the filtering process in step S17. Thus, the data processing using the mass spectrometry system 100 is completed.

As described above, the data processing method according to the present embodiment enables easy estimation of the composition between two peaks for which the compositions are unknown. In contrast, a data processing method of the related art needs to estimate the compositions of two molecules, whose compositions are unknown, in order to estimate the composition between the two molecules. The data processing method of the related art further needs to estimate the composition between the peaks of two molecules from combinations of the estimated compositions of the two molecules. This causes not only an enormous number of composition candidates but also difficulty in filtering candidates.

In the data processing method according to the present embodiment, when the composition of one of two molecules is known, the composition of the known molecule is combined with composition candidates between the peaks of the two molecules obtained by using the above-described data processing method. Thus, the composition of the remaining unknown molecule may be estimated. In addition, the range for composition estimation is made smaller. Therefore, the number of combinations of atoms may be decreased, enabling candidates to be easily filtered.

Figure 7:
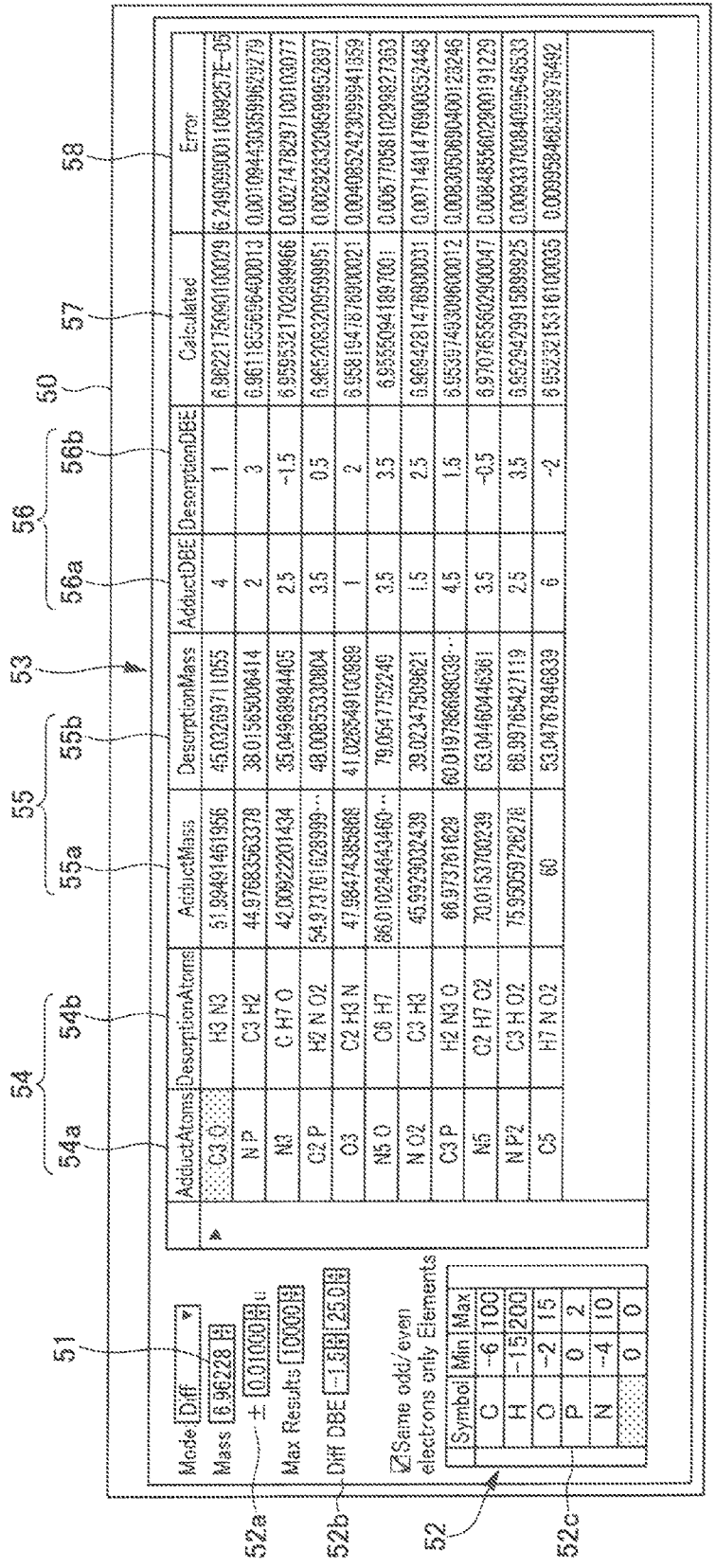
FIG. 7 is a diagram illustrating an exemplary display displayed on a display device of a mass spectrometry system according to an exemplary embodiment.

FIG. 7 is a diagram for describing an exemplary display of a result screen of the composition estimating process, which is displayed on the display device 5.

As illustrated in FIG. 7, an accurate-mass difference display area 51, a condition value display area 52, and a composition candidate list display area 53 are displayed on a display screen 50 of the display device 5. In the accurate-mass difference display area 51, the mass difference Δm/z between two molecules which is calculated in the computation process performed by the computation unit 11 in step S14 in the above-described data processing method is displayed.

In the condition value display area 52, the condition values which are set in step S11 in the above-described data processing method are displayed. In the condition value display area 52, an analysis error display area 52a and a DBE value display area 52b are displayed. In the analysis error display area 52a, the "error in mass (m/z)" is displayed. In the DBE value display area 52b, the "DBE value range" used in the filtering process is displayed. In the condition value display area 52, a filtering atom list 52c is also displayed. In the filtering atom list 52c, the element types used in seeking a combination of atoms, and the "minimum (Min)" and the "maximum (Max)" of the number of atoms of each element type are displayed.

In the composition candidate list display area 53, the result of the composition estimating process in the above-described data processing method is displayed. In the composition candidate list display area 53, a composition candidate atom list 54, a composition candidate accurate mass list 55, a composition candidate DBE value list 56, an estimated mass difference display area 57, and an error display area 58 are displayed.

In the composition candidate atom list 54, combinations of atoms which are obtained through composition estimation using the above-described data processing method are displayed. The composition candidate atom list 54 has an adduct-atom subset list 54a and a desorption-atom subset list 54b. In the adduct-atom subset list 54a, the subset of adduct atoms in each combination of atoms obtained through composition estimation is displayed. In the desorption-atom subset list 54b, the subset of desorption atoms in each combination of atoms obtained through composition estimation is displayed.

The composition candidate accurate mass list 55 has an adduct-atom subset accurate mass display area 55a and a desorption-atom subset accurate mass display area 55b. In the adduct-atom subset accurate mass display area 55a, the accurate mass of each subset of adduct atoms is displayed. In the desorption-atom subset accurate mass display area 55b, the accurate mass of each subset of desorption atoms is displayed.

In the composition candidate DBE value list 56, the DBE values calculated in step S21 in the above-described filtering process are displayed. The composition candidate DBE value list 56 has an adduct-atom subset DBE value display area 56a and a desorption-atom subset DBE value display area 56b. In the adduct-atom subset DBE value display area 56a, the DBE value of each subset of adduct atoms, that is, the DBE value of each subset of positive-number atoms is displayed. In the desorption-atom subset DBE value display area 56b, the DBE value of each subset of desorption atoms, that is, the DBE value of each subset of negative-number atoms, is displayed.

In the estimated mass difference display area 57, the difference (hereinafter referred to as the "estimated mass difference") between the accurate mass of the corresponding subset of adduct atoms and the accurate mass of the corresponding subset of desorption atoms in each combination of atoms obtained through composition estimation is displayed. The estimated mass difference is calculated by the computation unit 11 or the seeking unit 12. In the error display area 58, the error of each estimated mass difference, which is displayed in the estimated mass difference display area 57, with respect to the mass difference Δm/z, which is calculated by the computation unit 11, is displayed. As the error, the difference between the mass difference Δm/z and the estimated mass difference, the ratio of the estimated mass difference to the mass difference Δm/z, or the like is used. The error is calculated by the computation unit 11 or the seeking unit 12.

An exemplary display displayed on the display screen of the display device 5 is not limited to the display illustrated in FIG. 7. For example, only the composition candidate list display area 53 may be displayed. Further, in the composition candidate list display area 53, only the composition candidate atom list 54 and the error display area 58 may be displayed. On the display screen 50 of the display device 5, other various display examples are displayed. In addition, without performing the filtering process, all of the combinations of atoms which are found by the seeking unit 12 may be displayed as the processing result on the display device 5.

The present invention is not limited to the embodiment described above and illustrated in the drawings. Various changes may be made without departing from the gist of the invention described in the claims.

In the exemplary embodiment described above, the example of application of the filtering process using DBE values is described. The filtering process is not limited to this. For example, a hydrogen-carbon ratio may be used in the filtering process. Alternatively, the ratio between the number of desorption atoms and the number of adduct atoms may be used in the filtering process. Other various filtering methods may be applied.

What is claimed is:

1. A mass spectrometry data processing apparatus comprising:
    a computation unit that calculates a mass difference between peaks of two molecules selected from mass spectrum data or obtains the mass difference; and
    a seeking unit that estimates a combination of atoms between the peaks of the two molecules, the estimation being performed in a range of the mass difference,
    wherein the seeking unit seeks the combination of atoms, the combination having a mass difference matching the mass difference between the peaks of the two molecules, the mass difference of the combination being a mass difference between a set of atoms desorbed from a first molecule of the two molecules and a set of atoms added to the first molecule.

2. The mass spectrometry data processing apparatus according to claim 1,
    wherein the seeking unit seeks the combination of atoms by using a preset element type and a range from a minimum to a maximum of a number of atoms of the preset element type, and
    wherein the minimum is capable of being set to a number equal to or less than 0.

3. The mass spectrometry data processing apparatus according to claim 1, further comprising:

a filtering unit that filters the combination of atoms, the combination being found by the seeking unit.

4. The mass spectrometry data processing apparatus according to claim 3,
wherein the filtering unit performs the filtering process in accordance with a degree of unsaturation of a combination of desorption atoms and a degree of unsaturation of a combination of adduct atoms.

5. A mass spectrometry system comprising:
a mass spectrometer that performs mass spectrometry on a sample and generates mass spectrum data; and
a mass spectrometry data processing apparatus that obtains the mass spectrum data from the mass spectrometer,
wherein the mass spectrometry data processing apparatus comprises:
a computation unit that calculates a mass difference between peaks of two molecules selected from the mass spectrum data or obtains the mass difference, and
a seeking unit that estimates a combination of atoms between the peaks of the two molecules, the estimation being performed in a range of the mass difference,
wherein the seeking unit seeks the combination of atoms, the combination having a mass difference matching the mass difference between the peaks of the two molecules, the mass difference of the combination being a mass difference between a set of atoms desorbed from a first sample of the two molecules and a set of atoms added to the first sample.

6. A method for processing mass spectrometry data, the method comprising:
calculating a mass difference between peaks of two molecules selected from mass spectrum data or obtaining the mass difference; and
estimating a combination of atoms between the peaks of the two molecules, the estimation being performed in a range of the mass difference,
wherein, in the estimation, the combination of atoms is sought, the combination having a mass difference matching the mass difference between the peaks of the two molecules, the mass difference of the combination being a mass difference between a set of atoms desorbed from a first molecule of the two molecules and a set of atoms added to the first molecule.

* * * * *